United States Patent
Katingari et al.

(10) Patent No.: US 8,436,729 B2
(45) Date of Patent: *May 7, 2013

(54) PULSE WIDTH CODING WITH ADJUSTABLE NUMBER OF IDENTIFIER PULSES BASED ON CHANGE IN HEART RATE

(75) Inventors: Karthik H. Katingari, Milpitas, CA (US); Thomas Ying-Ching Lo, Fremont, CA (US)

(73) Assignee: Salutron, Inc., Fremont, CA (US)

( * ) Notice: Subject to any disclaimer, the term of this patent is extended or adjusted under 35 U.S.C. 154(b) by 425 days.

This patent is subject to a terminal disclaimer.

(21) Appl. No.: 12/819,892

(22) Filed: Jun. 21, 2010

(65) Prior Publication Data

US 2011/0205063 A1    Aug. 25, 2011

Related U.S. Application Data

(63) Continuation-in-part of application No. 12/711,114, filed on Feb. 23, 2010.

(51) Int. Cl.
*G08B 1/08* (2006.01)

(52) U.S. Cl.
USPC .................................................. 340/539.12

(58) Field of Classification Search ............ 340/539.12, 340/573.1, 870.24, 13.24, 539.1; 600/519, 600/520, 523; 375/237, 238
See application file for complete search history.

(56) References Cited

U.S. PATENT DOCUMENTS

| | | | |
|---|---|---|---|
| 5,611,346 A | 3/1997 | Heikkila et al. | |
| 5,632,279 A | 5/1997 | Heikkila | |
| 5,738,104 A | 4/1998 | Lo et al. | |
| 5,743,269 A * | 4/1998 | Okigami et al. | 600/509 |
| 5,876,350 A * | 3/1999 | Lo et al. | 600/519 |
| 6,332,094 B1 * | 12/2001 | Gorman | 600/520 |
| 6,449,509 B1 | 9/2002 | Park et al. | |
| 6,473,008 B2 | 10/2002 | Kelly et al. | |
| 6,496,546 B1 | 12/2002 | Allpress et al. | |

(Continued)

FOREIGN PATENT DOCUMENTS

| | | |
|---|---|---|
| JP | 62091876 A | 4/1987 |
| WO | 9641290 | 12/1996 |

OTHER PUBLICATIONS

CHA-CO International Company Limited, Wireless Digital Heart Rate Belt, CH9005 Kit, p. 1-9, Jun. 23, 2009.

(Continued)

*Primary Examiner* — Phung Nguyen

(74) *Attorney, Agent, or Firm* — Vierra Magen Marcus LLP

(57) ABSTRACT

A monitor provides a wireless signal with respective pulses, based on a heartbeat, repetitive physical movement, or other repetitive bodily action of a user. The pulses include longer duration pulses whose duration identifies the monitor, and distinguishes it from other monitors which may provide crosstalk interference. The longer duration pulses are interspersed among short duration pulses to reduce power consumption. The pulses are transmitted in successive cycles, where the number of the longer duration pulses is set adaptively in each cycle based on a detected rate, or rate of change, of respective instances of the bodily action. A receiver unit processes the signal to determine a rate of the bodily action and provide a corresponding output. The receiver unit can synchronize with two or more consecutive longer duration pulses. The pulse duration can be fixed or determined dynamically, e.g., non-deterministically.

20 Claims, 10 Drawing Sheets

U.S. PATENT DOCUMENTS

| | | |
|---|---|---|
| 6,961,374 B2 | 11/2005 | Chen |
| 7,030,735 B2 * | 4/2006 | Chen .................... 340/323 R |
| 7,129,835 B2 | 10/2006 | Nikkola |
| 2005/0135039 A1 | 6/2005 | Klemetti |
| 2006/0247549 A1 | 11/2006 | Chan |
| 2007/0176819 A1 | 8/2007 | May |
| 2009/0043217 A1 | 2/2009 | Hui et al. |
| 2010/0070669 A1 | 3/2010 | Johnson et al. |
| 2010/0097259 A1 | 4/2010 | Zhang |

OTHER PUBLICATIONS

Non-Final Office Action dated Feb. 15, 2013, U.S. Appl. No. 12/711,114 filed Feb. 23, 2010.

* cited by examiner

Fig. 3A        Fig. 3B
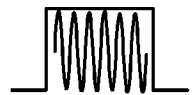 
Fig. 4A
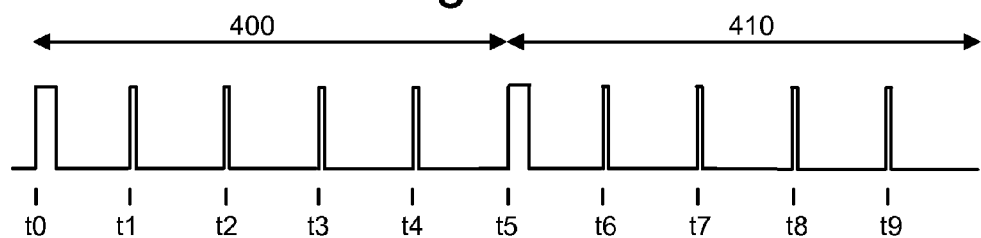
Fig. 4B
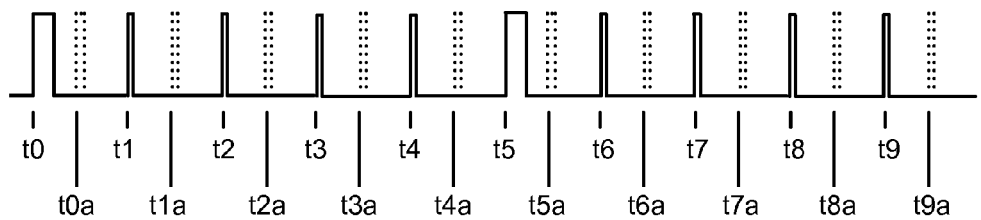
Fig. 4C
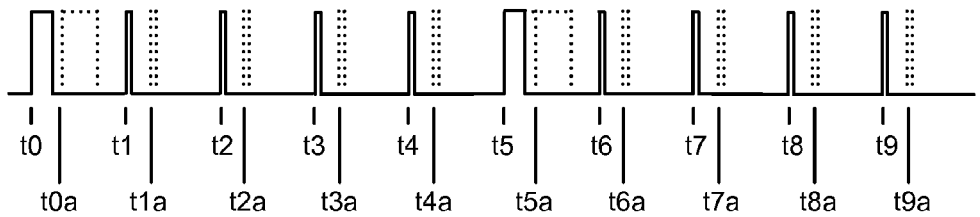

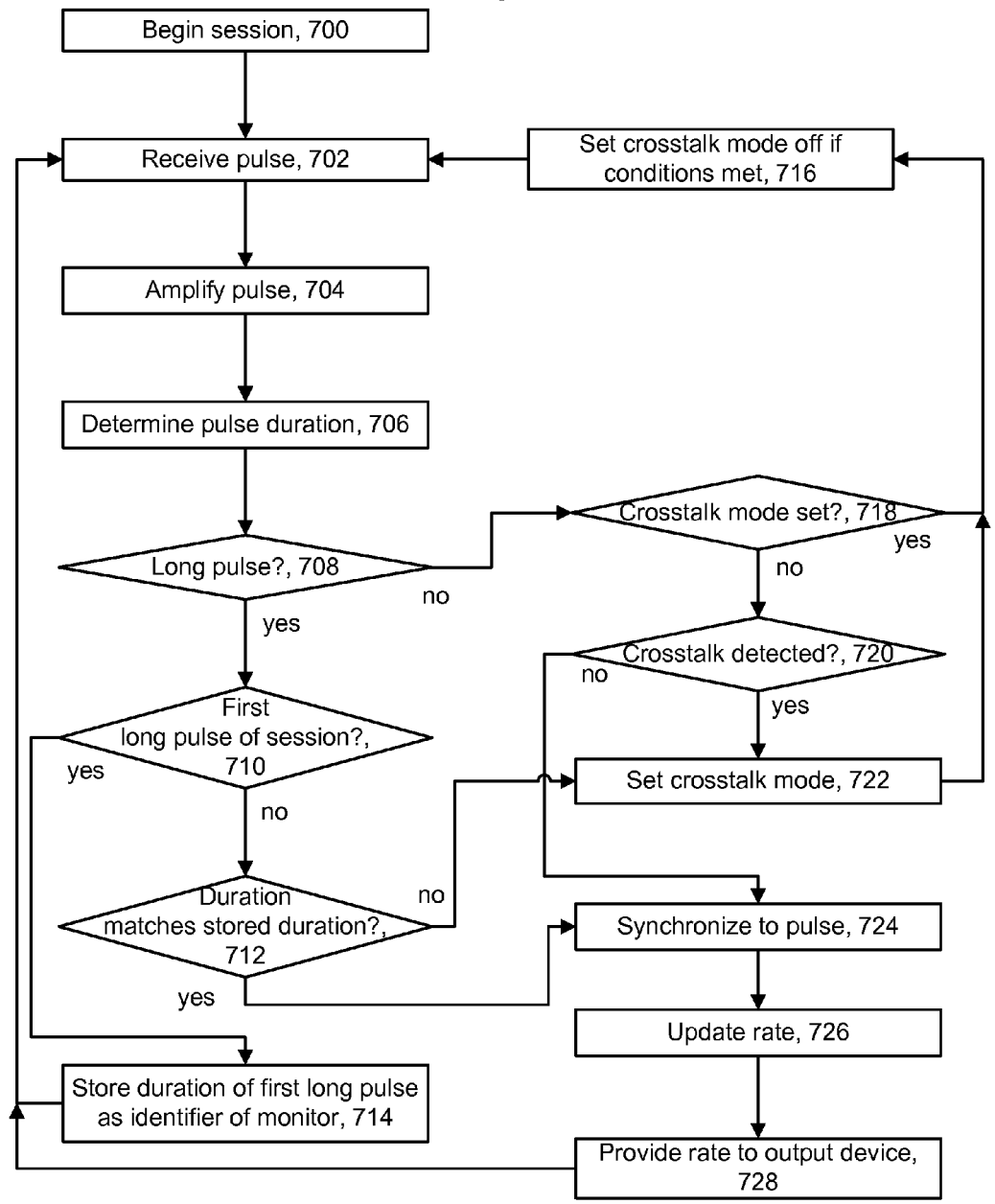

Fig. 11A
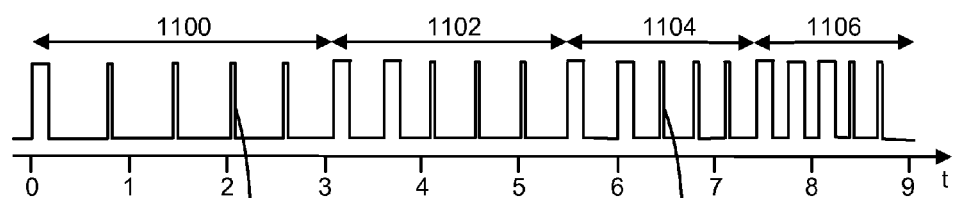
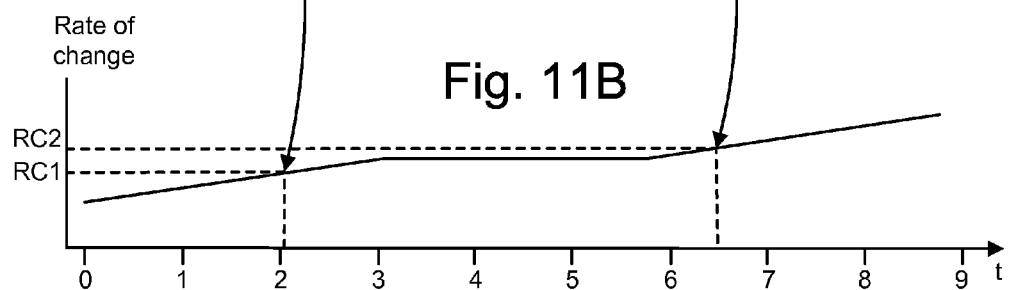
Fig. 11B

PULSE WIDTH CODING WITH ADJUSTABLE NUMBER OF IDENTIFIER PULSES BASED ON CHANGE IN HEART RATE

CROSS-REFERENCE TO RELATED APPLICATIONS

This application is a continuation-in-part of U.S. patent application Ser. No. 12/711,114, filed Feb. 23, 2010, titled "Pulse Width Coding For Interference-Tolerant Telemetric Signal Detection" to Katingari et al., published as U.S. 2001/0205051 on Aug. 25, 2001, incorporated herein by reference.

BACKGROUND

Wireless monitors are commonly used during exercise, athletic competitions, medical tests and other activities. For example, a heart rate monitor can be worn by a user, contacting the user at a suitable location such as the chest or wrist. A chest-worn monitor may detect an electrocardiogram (EKG) signal of the user's heart, each time a heart beat occurs, and transmit a corresponding pulse in a wireless signal to a receiver unit, where the signal is further processed to determine the heart rate. The receiver unit typically includes a display device which displays the heart rate to the user or other person. For example, the receiver unit can be worn on the user's wrist, provided in a console or other unit which is mounted to an exercise device such as a treadmill or bicycle, or provided in a portable or stationary device which is monitored by an athletic trainer, medical personnel or others.

In addition to monitoring of a heart rate, monitors are available for monitoring other bodily actions, such as breathing, or repetitive physical movements which are performed by a user during exercise, such as steps taken while running, or pedal revolutions during bicycling, and so forth. However, when wireless monitors are used in the same location, crosstalk can occur, preventing the receiver unit from accurately determining a rate at which the bodily action is performed. Other noise sources can also prevent the receiver unit from distinguishing the signal from a monitor. To this end, techniques have been developed for encoding additional identifying data onto the wireless signal. However, the existing approaches have drawbacks such as increased cost, power consumption, and complexity and susceptibility to additional sources of electromagnetic interference.

SUMMARY

A user-worn monitor, receiver unit and associated methods are provided for interference-tolerant telemetric signal detection.

In one embodiment, a user-worn monitor includes an amplifier circuit which receives a signal regarding a bodily action of a user and provides a corresponding amplified signal, a microcontroller associated with the amplifier circuit, and a transmitter associated with the microcontroller and the amplifier circuit. The transmitter provides a wireless signal based on the amplified signal. The wireless signal includes respective pulses in successive cycles, where each respective pulse is generated when a respective instance of the bodily action is detected, and the respective pulses include identifier pulses which each have a duration which is set in response to the microcontroller to identify the user-worn monitor, interspersed among other pulses, and a number N of the identifier pulses in each cycle is set adaptively based on the respective instances of the bodily action, where $N \geq 1$. For example, the number of the identifier pulses in each cycle can be set adaptively based on a detected rate of the respective instances of the bodily action, or based on a detected rate of change of the respective instances of the bodily action. Each respective instance of the bodily action can be a heartbeat, or a repetitive physical movement performed by the user during exercise.

In another embodiment, a method for transmitting a wireless signal from a user-worn monitor includes receiving a signal regarding a bodily action of a user and providing a corresponding amplified signal. The method further includes, based on the amplified signal, providing a wireless signal which includes respective pulses in successive cycles, where each respective pulse is generated when a respective instance of the bodily action is detected. The respective pulses include identifier pulses which each have a duration which identifies the user-worn monitor, interspersed among other pulses, and a number N of the identifier pulses in each cycle is set adaptively based on the respective instances of the bodily action, where $N \geq 1$.

In another embodiment, a receiver unit includes a receiver circuit which receives a wireless signal from a user-worn monitor. The wireless signal includes respective pulses generated by the user-worn monitor, where each respective pulse is generated when a respective instance of a bodily action of the user is detected, and the respective pulses include identifier pulses which each have a duration which identifies the user-worn monitor, interspersed among other pulses. The respective pulses are in successive cycles, where a number $N \geq 2$ of the identifier pulses in each cycle varies based on the respective instances of the bodily action. An amplifier circuit is associated with the receiver circuit, and provides an amplified signal based on the wireless signal. A microprocessor is associated with the amplifier circuit, and processes the amplified signal to interpret the duration of each of the identifier pulses as an identifier of the user-worn monitor. In each cycle, the microprocessor: (a) synchronizes with the identifier pulses, and (b) determines a rate of the bodily action based on: (i) time intervals between the identifier pulses in each cycle and (ii) a number of the other pulses between each of the identifier pulses. An output device is associated with the microprocessor, and provides an output based on the rate of the bodily action.

Corresponding methods may also be provided, along with a tangible processor-readable medium which stores code which is executable by a microprocessor to perform the methods described herein.

BRIEF DESCRIPTION OF THE DRAWINGS

FIG. 3A depicts an example long burst which is transmitted by a monitor.

FIG. 3B depicts an example short burst which is transmitted by a monitor.

FIG. 4A depicts a time line of a wireless signal transmitted by a monitor, where a single long pulse is used in a cycle.

FIG. 4B depicts a time line of the wireless signal of FIG. 4A with the addition of crosstalk of short pulses.

FIG. 4C depicts a time line of the wireless signal of FIG. 4A with the addition of crosstalk of long and short pulses.

FIG. 7 depicts an example method performed by the receiver unit of FIG. 1.

FIG. 11A depicts a time line of a wireless signal transmitted by a monitor, where a number of long pulses used in a cycle is adjustable based on a rate of change of a bodily action.

FIG. 11B depicts a rate of change of a bodily action, consistent with FIG. 11A.

DETAILED DESCRIPTION

Difficulties which are encountered by the presence of crosstalk and other forms of interference in a wireless signal are overcome to enable accurate communication between a user-worn monitor and an associated receiver unit. At the same time, advantages are achieved with regard to cost, power consumption, complexity and susceptibility to electromagnetic interference.

Figure 1:
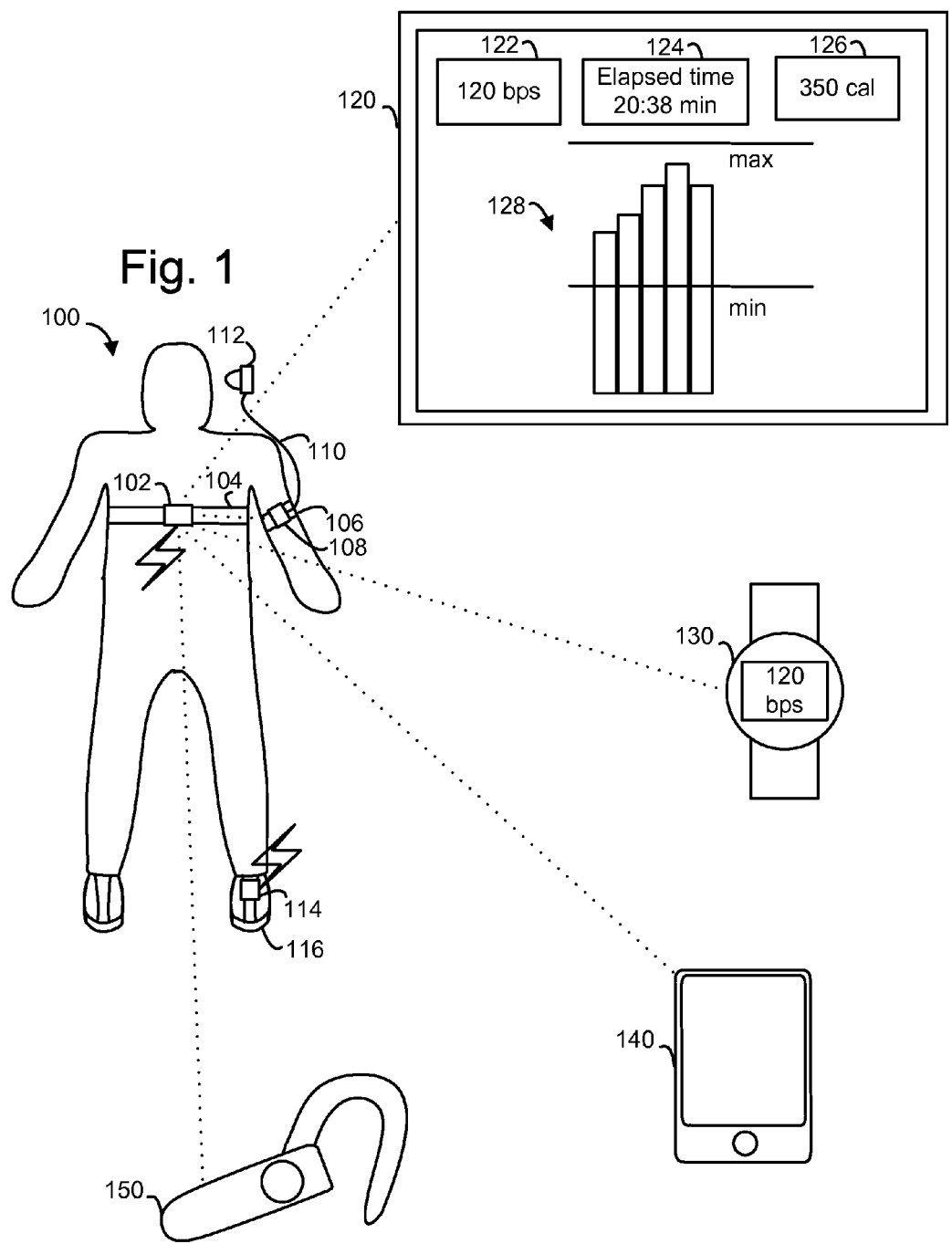
FIG. 1 depicts an example environment in which a monitor and a receiver unit are used.

FIG. 1 depicts an example environment in which a monitor and a receiver unit are used. Monitors can be used in a variety of environments. A typical application involves a user who is exercising for fitness or medical testing. Generally, a monitor can detect repetitive bodily actions. These include physiological actions such as a heart beating and breathing. A beating heart generates a low level of electrical activity in an EKG signal which can be detected by electrodes of a monitor, when the electrodes are held in contact with the user's skin. For example, the monitor 102 can be secured to an elastic strap 104 so that electrodes on the back side of the module are held against, e.g., the user's chest, back, or other portion of the torso. A heart beat can be detected by other approaches as well. For example, a monitor may use transmit ultrasonic signals into the user's body in a location of an artery, such as the radial artery in the wrist, and detect the reflected signal. Variations in the reflected signal due to blood flow in the artery can be correlated with a heart rate. Similarly, a breathing or respiration rate can be detected by a chest strap which continuously measures an extent to which it expands and contracts. Or, typically in a medical environment, a motion sensor can measure movement of the chest to determine respiration rate.

It is also useful to measure repetitive bodily actions such as repetitive physical movements which are performed by a user during exercise, such as steps taken while walking or running, pedal revolutions during bicycling, and so forth. Other examples include jump rope skips, and bodily action related to calisthenics such as lunges, jumping jacks, sit-ups, stomach crunches, push-ups, pull-ups, squats, calf-raises, toe touches, and dips. Other examples of repetitive bodily actions include muscle movements performed during weight training, such as leg or arm curls, bench presses, and some of the calisthenics which can be performed using weights.

For instance, a pedometer or step counter can be worn on the user's belt to detect repeated movements which are performed during walking or running. A pedometer typically employs a mechanical or electrical sensor, such as a microelectromechanical system (MEMs) inertial sensor. Wrist worn devices are also available which use an accelerometer to count repetitive movements during weight training, such as sets and repetitions. For example, a set may include ten repetitions. An example is the POLAR F55®. Similarly, monitors which can be worn on top of a shoe, such as monitor 114 are available. An example is the POLAR S1 FOOTPOD®. In this product, an inertial sensor and DSP (digital signal processor) provide real time running speed, pace and distance. Such a product can be used during running or cycling, for instance. Monitors which are built in to a shoe or clothing are also available. Examples are provided by products under the brand of ADIDAS®-POLAR® PROJECT FUSION™. The techniques provided herein can be incorporated into products of these types, among others.

In the example provided, the user has a monitor 114 worn on his shoe 116 as well as the chest-worn monitor 102. The monitors 102 and 114 transmit wireless signals which indicate when a repetition of the monitory bodily activity has occurred. For example, the monitor 102 as a heart rate monitor can transmit a pulse or burst each time a heart beat is detected. In one approach, a pulse can include a signal modulated at a relatively low frequency of 5.3 kHz, or more generally, between 4.8 kHz and 5.8 kHz. Such low frequency signals are advantageous since they do not typically require approval by a government agency such as the FCC in the United States.

High frequency signals can also be used. An example is a 2.4 GHz signal. Such high frequency signals require a faster processor and thus may be more expensive and consume more power, and government approval may be required. Also, unlike low frequency signals, they are also susceptible to interference from electronic devices such as microwave ovens, cell phones, computers and wireless local area networks (WLAN) base stations used in computer networks.

The monitor 114 as a pace monitor can transmit a signal each time a step is detected. Similarly, the monitor 114 could detect a revolution of the user's feet, e.g., a chain ring revolution, on a stationary or moving bicycle as the user pedals while wearing the shoe 116.

A wireless signal transmitted from a monitor can be received at a receiver unit, where the signal is processed to provide an output in a visible and/or audible form for the user or other person. In some cases, the monitor transmits only and does not receive wireless signals or other signals while operating.

A console 120 is an example of a receiver unit. A console 120 can be mounted to exercise equipment such as a bicycle, treadmill, or stair climber machine, for instance, in a position in which it provides a display to the user 100. Or, the console 120 can be mounted or handheld, for use by another person such as an athletic trainer or medical personnel. In this example, the console has a display with a region 122 which provides a current heart rate, e.g., 120 beats per second (bps), a region 124 which indicates a elapsed exercise time, a region 126 which indicates a number of calories burned in the exercise session, and a region 128 which is a bar chart showing a history of the heart rate, e.g., over the past few minutes, relative to a target heart rate range which is between maximum (max) and minimum (min) levels. The console can also provide an audible output such as an alarm when the heart rate moves outside the target heart rate range, to signal to the user to move faster or slower.

Another example of a receiver unit is a wrist worn device 130 which provides an output in the form of a display of the current heart rate or other detected rate, for instance. An audible alarm or other output can also be provided as discussed. The receiver unit can be wrist worn, similar to a wrist watch, and may in fact have time keeping ability as well as the ability to provide an output based on the received wireless signal.

Another example of a receiver unit is a portable device 140 such as a cell phone, media player, personal digital assistance (PDA) or similar device. Such a device can be held in the user's hand or attached to the user's body, e.g., using a strap, or placed in a pocket of clothing worn by the user. The portable device 108 is held in an arm strap 106 as an example. The monitor 102 or 114 can communicate with the portable device 108 via a low frequency signal with the use of appropriate circuitry as described herein. The portable device 140 can provide a visual or audible output as discussed. In one approach, the user can receive an audible input from the portable device via an earphone such as an ear bud 112 which is connected by a wire 110 to the portable device 108. Such earphones are commonly used with portable media players. The audible output can include a synthesized voice which states the current heart rate at specified intervals, when the current heart rate is out of the target zone, or at other specified times.

Another example of a receiver unit is a wireless ear-worn device 150 which is similar to devices used to communicate with cell phones using Bluetooth (IEEE 802.15.1) transmissions. The monitor 102 or 114 can communicate with the ear-worn device 150 with the use of appropriate circuitry. Or, the monitor 102 or 114 can transmit a wireless signal to the portable device 140 such as a cell phone, where the portable device 140 in turn communicates with the wireless ear-worn device 150 to provide an audible output to the user 100, as discussed above. Many other variations are possible. Moreover, the wireless signal from a monitor can be received and processed by more than one receiver unit. In addition to real-time processing and updating of a heart rate or other parameter at a receiver unit, the receiver unit can record data from a monitor in a non-volatile memory such as a computer hard drive or flash memory for subsequent analysis.

Figure 2:
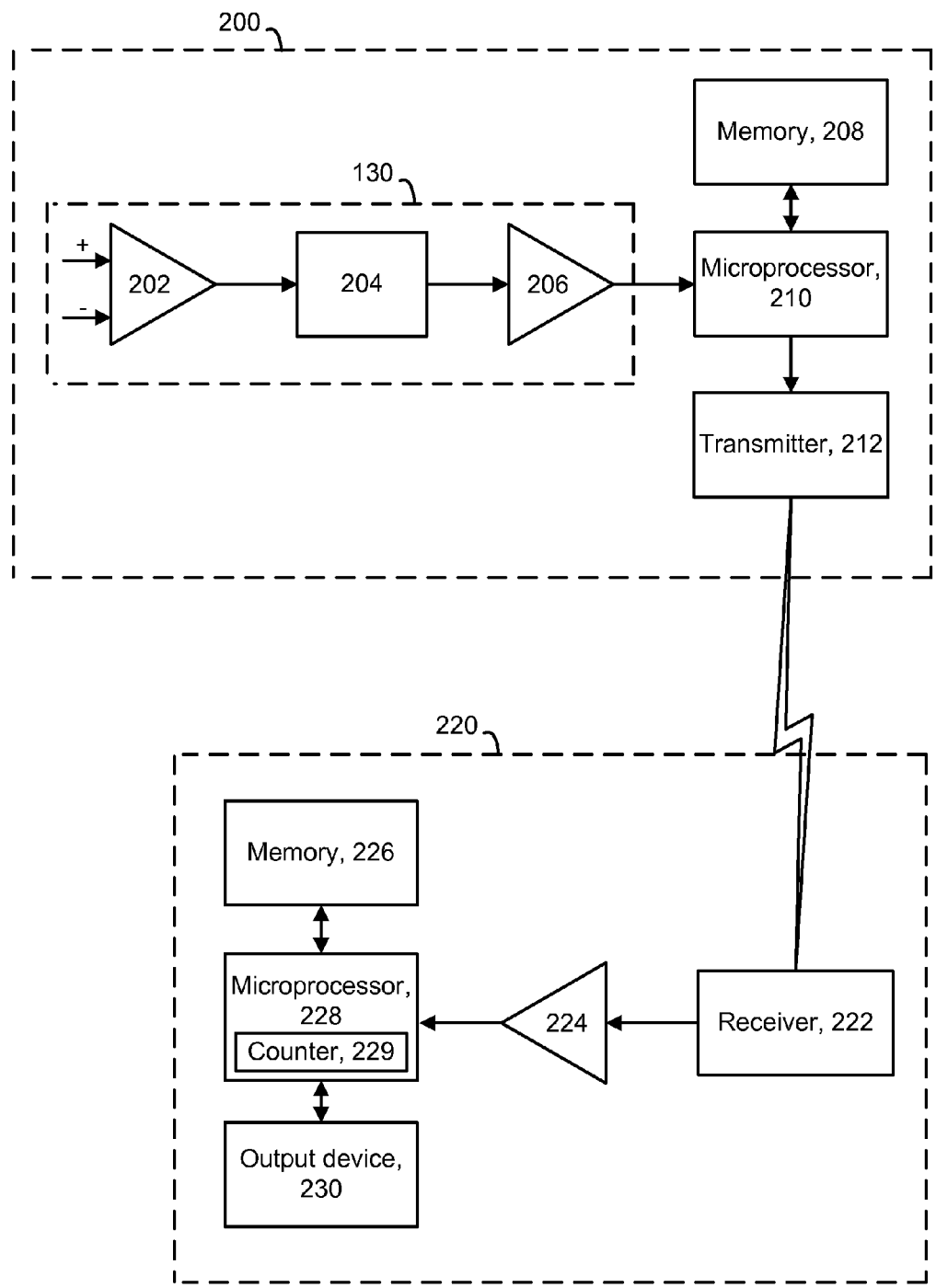
FIG. 2 depicts an example embodiment of a monitor and receiver unit.

FIG. 2 depicts an example embodiment of a monitor and receiver unit. A monitor 200 includes an amplifier circuit 130, which includes a differential amplifier or preamplifier 202, an amplifier/filter stage 204, and a final amplifier 206. In one implementation, the differential amplifier or preamplifier 202 receives an EKG signal of a user. The amplifier circuit 130 provides an amplified signal to a microprocessor 210. The microprocessor has a built-in A/D converter. The microprocessor samples and processes the amplified EKG signal to detect heart beats. Further details of such detection can be found, for instance, in U.S. Pat. No. 5,738,104 to Lo et al. and U.S. Pat. No. 5,876,350 to Lo et al., both of which are incorporated herein by reference. After a heart beat is detected, the microprocessor 210 will deliver a digital signal at each detected heart beat to a transmitter 212, which may include a transmitting coil and operate, e.g., by inductive or electromagnetic coupling. In one implementation, communication is one way from the microcontroller to the transmitter. The microprocessor 210 generates a digital burst signal, such as at 5.3 kHz, causing the coil in the transmitter to resonate and thereby transmit a wireless signal. The duration of the resonance and the corresponding pulse or burst which is transmitted is controlled by the microprocessor 210.

Thus, the transmitter can comprise an inductive resonator which provides each pulse in the wireless signal as an inductive burst, and the pulses generated by the monitor 200 each comprise an inductive burst, in one embodiment. The microprocessor 210 may access a memory 208 which includes code which is executable by the microprocessor 210. The memory 208 may include a tangible storage device such as a non-volatile memory, e.g., ROM, and a volatile memory, e.g., RAM, which store processor-readable code which is executed by one or more microprocessors to implement the functionality described herein.

As an option which reduces power consumption and cost, the output from the amplifier circuit 130 can be provided to a threshold detector. The threshold detector provides a digital output based on the level of the input. This digital output can be used to indicate the onset of a detected heart beat or other bodily action. In this case, no A/D conversion is needed. Microprocessor 210 can also run at a lower clock speed to save power.

The receiving unit 220 includes a receiver circuit 222, amplifier 224, microprocessor 228, memory 226 and output device 230. The microprocessor 228 may include a free running counter 229 which is used to select an identifier, as discussed below in connection with FIG. 6. The receiver circuit 220 may include coils which detect a magnetic field of the wireless signal and provide a corresponding signal to the amplifier circuit 224. In one approach, the amplifier circuit 224 includes a sensitive preamplifier followed by a signal amplifier. The amplified signal is processed by a microprocessor 228, which is responsive to code stored in a memory 226. The microprocessor can calculate a rate at which a bodily action of the user is performed based on a rate at which some or all of the pulses are received. The microprocessor provides a signal to an output device 230 to provide a visual and/or audible output as discussed.

FIG. 3*a* depicts an example long burst which is transmitted by a monitor. FIG. 3*b* depicts an example short burst which is transmitted by a monitor. Each burst is interpreted as a single pulse as indicated by the pulse-shaped envelope.

In one embodiment, the duration of a burst is used as an identifier of the monitor, and different durations can be used to identify different monitors. With this type of positive identification, crosstalk and other types of interference can be handled. A long burst represents a pulse or burst whose duration is noticeably longer than a nominal, short burst. A short burst can be 5-10 milliseconds (msec.) for instance, while a longer burst can range from 20-250 msec., for instance. The long burst can be 2× or more longer than the short burst. The upper limit of the long burst depends on the application. For heart beat detection, a heart rate of 30-240 bpm may be covered. 240 bpm, or 4 beats per second, translates to a period between beats of 250 msec. The duration of the long burst should be less than the period between detected bodily events. In practice, a longer burst uses more power so the long burst need not be at the upper allowable limit. A long burst should have a duration which allows the burst to be distinguished from a short burst and from other long bursts. As an example, a long burst can be, e.g., at least 5-10 msec. longer than a short burst.

As a result, a predefined set of different durations which are identifiers for different user-worn monitors can be provided and stored in the monitor and receiver unit. Additionally, a binary code word can be assigned to each duration. For example, with $2^5=32$ code words, and a 5 msec. difference between long pulses, long pulse durations of 10, 15, 20, ..., 155, 160, 165 msec. can be used in the predefined set. Corresponding example five-bit code words are 00000, 00001, 00010, ..., 11101, 11110, 11111, respectively.

FIG. 4A depicts a time line of a wireless signal transmitted by a monitor, where a single long pulse is used in a cycle. The long pulse is an identifier pulse because its duration is used by the receiver unit as an identifier of the monitor. In one approach, a cycle includes a predefined number N of pulses. One or more long pulses can be provided in each cycle, or in every nth cycle, where $n \geq 1$. Moreover, the monitor and receiver unit can be preconfigured with knowledge of the number of pulses per cycle. Two example cycles 400 and 410 are depicted. Time increases moving to the right hand side of the figure. The pulse sizes and shapes are not necessarily to scale. In this example, one long pulse is provided per cycle, at t0 and t5. Additionally, the long pulse is at the start of a cycle, although this is not required. In each cycle, the long pulse is followed by other, shorter pulses of equal duration, e.g., 5-10 msec. Four short pulses are used as an example at t1-t4 and t6-t9.

Another option is to use all long pulses in each cycle. However, using a minimal number of long pulses mixed or interspersed among short pulses allows a monitor to be identified by a receiver unit while minimizing power consumption by the monitor. Generally, a long pulse can be transmitted every X beats, Y consecutive times to allow the receiver unit to synchronize to the correct monitor. X and Y can be integers which are greater than or equal to one. As an alternative, one or more long pulses can be transmitted in response to the first detected bodily action after every Z seconds, as discussed in connection with FIG. 4D.

In FIG. 4A, it can be seen that the wireless signal does not contain an identifier of the user-worn monitor other than an identifier which is provided by the duration of the identifier pulses, e.g., at t0 and t5. Also, the wireless signal does not contain pulses generated by the monitor at times other than when the bodily action of the user is detected. This is true because the transmitter does not provide the wireless signal with pulses at times other than when the bodily action of the user is detected. This is advantageous since the use of additional pulses, at times other than when the bodily action of the user is detected, consume power. Moreover, the shorter pulses each have a duration which does not identify the monitor and which is less than the duration of the long pulses, which identifies the monitor.

FIG. 4B depicts a time line of the wireless signal of FIG. 4A with the addition of crosstalk of short pulses. Crosstalk can occur when two or more users who are wearing a common type of monitor are near one another, e.g., within a few feet. The receiver unit (subject receiver unit) which is intended to receive a wireless signal from a given monitor (subject monitor) also receives a wireless signal from one or more other monitors (crosstalk monitors) as undesired crosstalk. This can occur when users are exercising together, e.g., at stationary exercise equipment in a gym, or while jogging alongside one another in a group. A given receiver unit may experience different degrees of crosstalk at different times, as other users and their monitors move closer and away from the subject user and the subject monitor. In addition to crosstalk, other types of interference can be created by the user's environment, e.g., due to high voltage power lines, televisions, motor-driven exercise equipment, cell phones, and so forth. The subject receiver unit may be unable to process the wireless signal from the subject monitor, or provide an erroneous output, if the crosstalk cannot be handled. In this example, short crosstalk pulses from another monitor are indicated by dashed lines at t0a-t9a.

In some cases, a receiver unit can detect when crosstalk is present. For example, when the long pulse at t0 is received, the receiver unit can determine an expected time to receive a next pulse, particularly if information from previous pulses has been used to determine a current rate of detection of the bodily action. Typically, the time interval between successive pulses will be relatively uniform, so that an expected time interval at which a next pulse is received can be estimated with good accuracy based on the time interval at which the last pulse was received. Thus, knowing that a next pulse should be received at or near t1, the presence of the crosstalk pulse at t0a can be identified as crosstalk, and ignored, by a receiver unit. Another example technique to detect crosstalk involves detecting the amplitude of each pulse, where higher amplitude pulses are assumed to be from the subject monitor, based on the assumption that the subject monitor is closer to the subject receiver unit than the crosstalk monitor. See US patent application publication no. US2009/0043217 to Hui et al., published Feb. 12, 2009, and incorporated herein by reference, for further details.

In some cases, the crosstalk pulses may be sufficiently close to the pulses of the subject monitor so that the receiver unit cannot distinguish the correct pulses. In such cases, the microprocessor of the receiver unit can enter a special crosstalk mode in which it only synchronizes with the long pulses, but not the short pulses, to determine the rate of the bodily action. The rate can be determined knowing the time interval between the long pulses and the number of short pulses between the long pulses. For example, a rate based on the long pulses at t5 and t0, with four pulses between them, is 5 beats/(t5-t0). In this case, the rate is updated less often than every pulse. The microprocessor can continue to detect the short pulses, whether they are crosstalk or not, to determine when crosstalk is no longer present at a threshold level, and to return to another, baseline mode in which case the microcontroller of the receiver unit synchronizes with each pulse to update the rate.

A threshold level of crosstalk can be defined which the microcontroller uses to determine whether to change its operating mode. The threshold level may be met, e.g., if one or more crosstalk pulses are detected in one or more cycles, even if it is determined that they have highly inconsistent timing and therefore can be ignored. Or, the threshold level may be met if a specified number of crosstalk pulses are detected in a cycle, and this is repeated for a specified number of cycles. Or, the threshold level may be met if one or more crosstalk pulses are detected which render it impossible to accurately detect the short pulses in one or more cycles. Or, the threshold level may be met if one or more crosstalk pulses are detected which have a specified amplitude, such as an amplitude which is a specified portion of the non-crosstalk pulses. Or, the threshold level may be met if one or more crosstalk pulses are detected which have a discernible amplitude. Other definitions of the threshold level may be used as well.

The microprocessor can change back and forth between the crosstalk mode and the baseline mode as the level of crosstalk changes over time. In this way, the highest possible update rate is maintained whenever possible.

In this example, the monitor of the subject user provides a long pulse as an identifier in each cycle, while the crosstalk is provided by a crosstalk monitor which does not use a long pulse. Another example scenario, discussed next, involves both monitors using long pulses.

FIG. 4C depicts a time line of the wireless signal of FIG. 4A with the addition of crosstalk of long and short pulses. As before, the pulses from the given monitor are at t0-t9 and the pulses from the other monitor are indicated by dashed lines at t0a-t9a. As before, the presence of the crosstalk pulses can be identified as crosstalk by a subject receiver unit when they are received at an inconsistent time. In one approach, the rise of each pulse is interpreted as the received time of the pulse, so that long and short pulses are interpreted consistently, and a long pulse is not interpreted as having arrived later than it did. Also, by interpreting the rise of each pulse as the received time of the pulse, compatibility is provided with a receiver unit which does not distinguish a long pulse from a short pulse, or is otherwise blind to pulse width.

A further mechanism for detecting crosstalk is to compare the duration of each long pulse to the known duration which has been associated with the subject monitor. If the duration is inconsistent with the known duration, either shorter or longer by a specified margin such as 1-2 msec., the long pulse can be determined to be crosstalk. Moreover, a determination that crosstalk is present can be based on analysis of the duration and/or timing of more than one pulse. In this case, a pulse that appears to be crosstalk may not trigger the crosstalk mode in the microprocessor of the subject receiver unit until the determination is confirmed by one or more other pulses in the same cycle and/or one or more other cycles. A pulse that appears to be crosstalk can be ignored or skipped at the subject receiver unit for purposes of determining a rate of received pulses. The timing of the next pulse which does not appear to be crosstalk, with knowledge of the number of skipped pulses, can be used to determine the next updated of the rate, in one approach.

In some cases, a crosstalk pulse may overlap with a pulse from the subject monitor such that a pulse from the subject monitor is corrupted and appears to be longer than it is. In such cases, the enlarged pulse may be ignored by the subject receiver unit, and the next uncorrupted pulse used to determine the rate. Generally, crosstalk reduction is a probabilistic technique which attempts to account for the most probable scenarios.

Figure 4D:
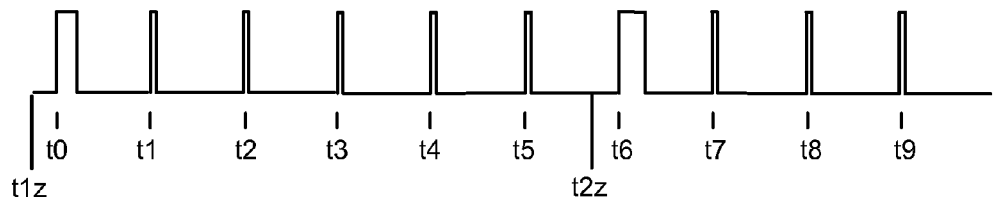
FIG. 4D depicts a time line of a wireless signal transmitted by a monitor, where a single long pulse is used after every Z seconds.

FIG. 4D depicts a time line of a wireless signal transmitted by a monitor, where a single long pulse is used after every Z seconds. Instead of transmitting a long pulse based on a pulse position within a cycle or based on a pulse count, one or more long pulses can be transmitted based on specific time intervals. Fixed or varying intervals can be used. In an approach which uses a fixed interval, a long pulse is transmitted based on a specified period such as every Z seconds. For example, assume a period begins at tz1, just before the long pulse at to, and Z seconds later occurs just before t6, at t2z. The period is t2z-t1z. In this case, the next pulse after t2z which is transmitted will be a long pulse, at t6. In this approach, the number of short pulses between long pulses can vary as the rate of the detected bodily action varies. In one approach, the heart rate is based on the temporal spacing of each pulse, including both the long and short pulses.

Figure 5A:
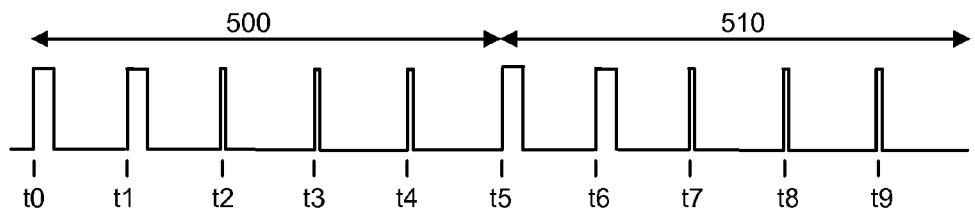
FIG. 5A depicts a time line of a wireless signal transmitted by a monitor, where two long pulses are used in a cycle.

FIG. 5A depicts a time line of a wireless signal transmitted by a monitor, where two long pulses are used in a cycle. By having multiple long pulses in a cycle, timing information can be gained faster by the receiver unit even when the presence of crosstalk renders undistinguishable the other, short pulses which are meant for the receiver unit. Thus, the receiver unit can synchronize sooner with the monitor. For example, long pulses are provided at t0 and t1 in a cycle 500, and at t5 and t6 in a cycle 510. Short pulses are provided at t2-t4 and t7-t9. The long pulses can be consecutive but this is not necessary as long as their relative positions (e.g., the number of short pulses between them, which is zero or more) is known. Here, once the long pulses at t0 and t1 are received, the interval between them indicates a rate, as well as the expected interval of the next pulse, which is a short pulse in this example. Thus, the rate can be determined right away, and the presence of a pulse which is inconsistent with the expected timing can be identified as crosstalk.

Figure 5B:
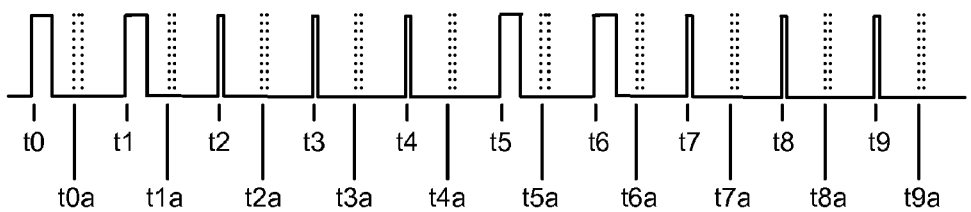
FIG. 5B depicts a time line of the wireless signal of FIG. 5A with the addition of crosstalk of short pulses.

FIG. 5B depicts a time line of the wireless signal of FIG. 5A with the addition of crosstalk of short pulses at t0a-t9a. Here, the crosstalk pulses can likely be identified and distinguished from the correct pulses, as discussed previously. If the crosstalk pulses cannot be distinguished, the microprocessor of the receiver unit can enter the crosstalk mode. In this case, the timing of the long pulses, combined with knowledge of the number of short pulses between the long pulses, can be used to update the rate when each long pulse is received.

Figure 5C:
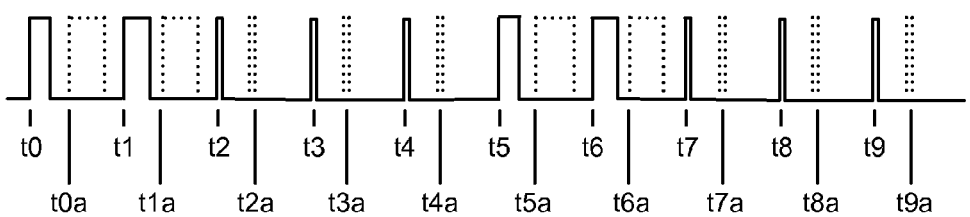
FIG. 5C depicts a time line of the wireless signal of FIG. 5A with the addition of crosstalk of long and short pulses.

FIG. 5C depicts a time line of the wireless signal of FIG. 5A with the addition of crosstalk of long and short pulses. In this example, the subject monitor and the crosstalk monitor both use two long pulses (e.g., of different durations) as identifiers in each cycle. As before, the pulses from the subject monitor are at t0-t9 and the pulses from the crosstalk monitor are indicated by dashed lines at t0a-t9a. As discussed before in connection with FIG. 4C, the timing of the pulses, as well as the duration of the long pulses, can be used to detect whether or not a threshold level of crosstalk is present.

Variations and combinations of the approaches in FIGS. 4A, 4D and 5A can also be used. For example, a transmission may switch between the approaches at different times. For instance, one or more cycles can be used which each have one long pulse, followed by one or more cycles which each have two or more consecutive pulses. Thus, the long pulses can appear consecutively and/or non-consecutively in a wireless signal.

Figure 6:
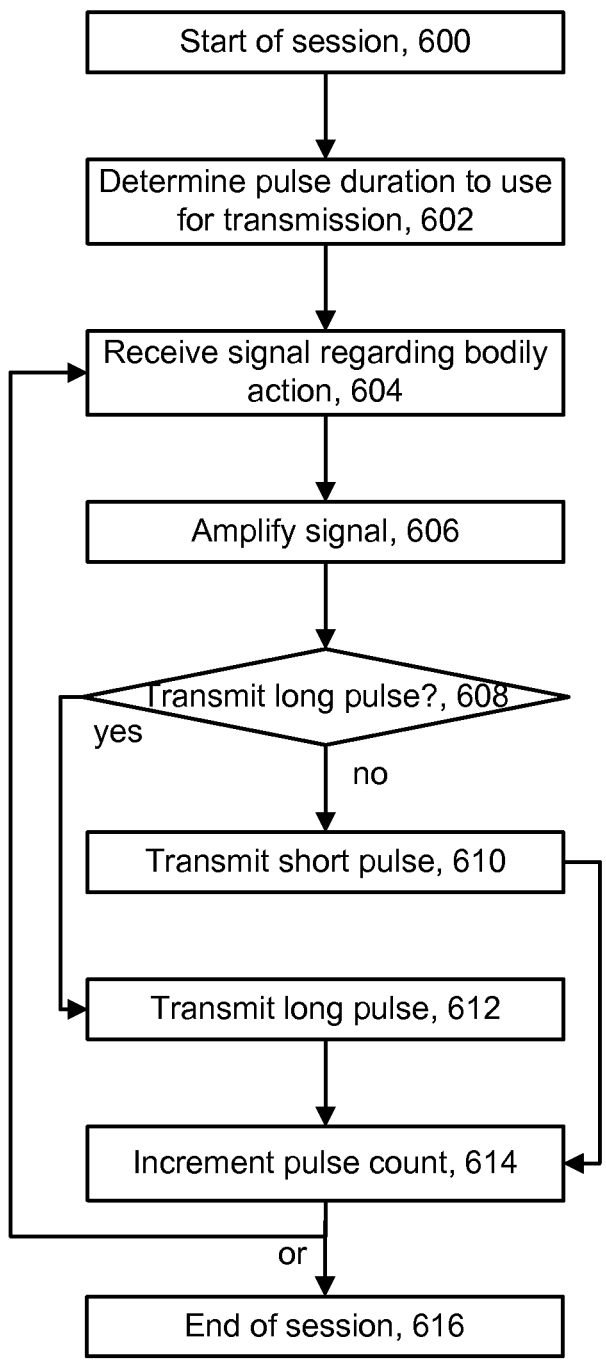
FIG. 6 depicts an example method performed by the monitor of FIG. 1.

FIG. 6 depicts an example method performed by the monitor of FIG. 1. A session such as an exercise session starts at step 600. This may occur when the user attaches the monitor to his or her body. For example, a chest-worn monitor may start transmitting when it is placed in contact with the user's skin and thereby picks up the EKG signal of the user. In some scenarios, no crosstalk is present when the session begins. For instance, a first user may be jogging along with a chest-mounted monitor and a wrist-mounted receiver unit. In this case, there is no problem with crosstalk and the receiver unit can quickly synchronize with the monitor. The first user then meets with a friend who also has a receiver unit synchronized to his monitor, and continues jogging with the friend. In this case, the friend's monitor may cause crosstalk to the receiver unit of the first user. However, this can be accommodated using the techniques provided herein. Moreover, the level of the crosstalk may fall below or rise above a threshold level as the users move further or closer apart, respectively.

Step 602 includes determining a pulse duration to use for transmission. A monitor may be hard-coded with a specific long pulse duration to use, or it may selected the duration from a predefined set of different durations which are identifiers for different user-worn monitors. For example, the predefined set can be stored in the memory 226 of the receiver unit (FIG. 2). The microcontroller can set the duration non-deterministically by accessing the memory to select one of the durations from the predefined set of different durations.

In one approach, the microprocessor uses a free running counter 229, which is a counter than is constantly up from zero, for instance, until a maximum value is reached, at which time the counter restarts the counting. Such a counter can be implemented in hardware, for instance, and provide a value which is mapped to one of the available durations. The value of the count can be stored and accessed from a memory register. A non-deterministic selection of a duration includes a random or pseudo-random selection. Other possible techniques for selecting a duration use a random number generator which is realized by hardware and/or software. A random number generator can be implemented by a software algorithm that runs continuously with an output number that changes randomly. Another approach is to determine the long pulse duration by counting random events such as a start or end of a session. Another approach is to determine the long pulse duration based on a rate acquisition time or the rate itself. For example, when a user ends an exercise session and removes the monitor, the monitor can record and store the current rate based on the timing between the last two consecutive transmitted pulses. This stored value can be accessed when a new session is later started and used as a seed input to a random number generator, for instance, to determine a value which is mapped to one of the predefined available pulse durations.

As discussed, various transmission patterns can be used. Generally, the transmission includes long pulses interspersed among other, short pulses. The long pulses can appear consecutively and/or non-consecutively. A transmission pattern can be used based on repeated cycles, where each cycle has the same pattern, and one or more long pulses are in predefined positions within a cycle, interspersed among the short pulses. The one or more long pulses in a cycle can be at the start of a cycle or other relative position within a cycle, in a cycle-based pattern. Or, a time-based pattern can be used, e.g., as discussed in connection with FIG. 4D, where long pulses are transmitted at specified time intervals, such as periodically, interspersed among the short pulses. When a time for transmitting a long pulse is reached, the long pulse is transmitted when the next bodily action is detected.

At step 604, the monitor receives a signal regarding a bodily action, such as an EKG signal indicating that a heart beat has occurred, or a signal from a pedometer which indicates that the user has taken a step or performed an instance, e.g., occurrence, of a repetitive physical movement during exercise. For example, the repetitive movement may be jogging, where an instance of the movement is each step. Where the repetitive bodily action is the heart beating, an instance of the bodily action is one heart beat. At step 606, the monitor amplifies the signal. At decision step 608, if a condition is met for transmitting a long pulse, the monitor transmits a long pulse, at step 612. The condition can be based on a cycle-based pattern or a time-based pattern, for instance, as discussed.

At decision step 608, if the condition for transmitting a long pulse is not met, the monitor transmits a short pulse, at step 610. At step 614, a pulse counter is incremented. The pulse counter can be used to track the current position within a cycle and to determine when to start a new cycle. The monitor waits to receive the next signal regarding the bodily action, at step 604, or the session ends at step 616.

A session can end when the user takes the monitor off, or manually turns the monitor off, for instance. A timeout period such as several seconds may be enforced by the monitor and/or receiver unit before the session of exercise is determined to end, at which time the identification of the monitor may be discarded. In a subsequent new session, the monitor can select another pulse duration as its identifier, and the receiver unit again identifies the monitor based on the newly-chosen duration of the identifier pulses. For example, a session can be defined as a time period in which a user wears a chest strap, where the end of the session occurs when the user removes the chest strap. The microcontroller of the monitor can be configured so that the intermittent disconnection of the chest strap does not create a new session. For example, if the removes the chest strap but reattaches it within next "x" seconds (e.g., 15, 30 or 60 seconds), the session is maintained, but if there is a gap of more than "x" seconds, a new session is started and assigned a new long pulse width.

In this case, the pulse duration and therefore the monitor identifier is dynamic. Or, the pulse duration may be hard-coded into a matched set of a monitor and a receiver unit, and different respective pulse durations may be hard-coded into different respective matched monitor-receiver unit sets.

The communication may be one-way from the monitor to the receiver unit so that the long pulse duration is not changed once a session begins.

FIG. 7 depicts an example method performed by the receiver unit of FIG. 1. The receiver unit begins a session at 700, such as when it is powered on. As an example, a receiver unit which is mounted to exercise equipment may begin a session and exit a sleep mode when the user starts to move on the exercise equipment, such as walking on a treadmill. At step 702, a pulse is received from the monitor. Each pulse represents a respective instance of the bodily action which is monitored. As mentioned, the bodily action can be a heartbeat. Or, each respective instance of the bodily action can be a respective instance of a repetitive physical movement performed by the user during exercise.

At step 704, the pulse is amplified. At step 706, the pulse duration is determined, e.g., as the time interval between the leading and trailing edges of the pulse. At decision step 708, if the pulse is a long pulse, decision step 710 determines if it is the first long pulse of the session. If it is the first long pulse of the session, its duration is stored as an identifier of the monitor at step 714. Data which represents the duration itself as a time value can be stored, or the duration can be mapped to a code word which is stored. An additional check can be made to ensure that the duration is consistent with a predefined set of durations which are available identifiers of different monitors. For example, the duration may be required to match, within a tolerance, one of the available durations.

At decision step 710, if the long pulse is not the first long pulse of the session, a decision step 712 determines if the duration matches a previously-stored duration within a tolerance of, e.g., +/−1-2 msec. If there is a match, the microcontroller synchronizes to the pulse at step 724. That is, the microcontroller uses the timing of the pulse. At step 726, the rate of the bodily action is updated based on the pulse, and at step 728, the newly-updated rate is provided to an output device. A next pulse is then received at step 702.

If decision step 712 determines that the pulse duration does not match the stored duration, a crosstalk mode can be set for the microprocessor at step 722, in one possible approach. As mentioned previously, various criteria can be used to determine whether a threshold level of crosstalk is detected and to decide whether or not to set a crosstalk mode to accommodate the crosstalk. The mode can switch from the crosstalk mode back to the baseline mode if certain conditions are met, at step 716, such as the crosstalk level falling below a threshold level. Switching between modes may be controlled so that it does not occur too frequently. For example, mode switching may occur only after a time interval has passed or a minimum number of pulses have been detected. A next pulse is then received at step 702.

If decision step 708 determines that the current pulse is not a long pulse, decision step 718 determines if the crosstalk mode has been previously set. If the crosstalk mode is set, steps 716 and 702 follow. In this case, the microprocessor does not synchronize to the short pulse so that its timing information is not used to update the rate. If the crosstalk mode is not set at decision step 718, decision step 720 determines if a threshold level of crosstalk is currently detected. If the threshold level of crosstalk is detected, the crosstalk mode is set at step 722. If decision step 720 determines that the threshold level of crosstalk is not detected, steps 724, 726 and 728 are performed as discussed.

Generally, when the receiver unit is powered on and the monitor is transmitting, a time period of a few seconds may pass before the receiver unit synchronizes to the monitor and outputs a rate. During this time period, or after, the receiver unit sees a long duration pulse and uses it as an identifier of the monitor, and continues its synchronization with that monitor.

Figure 8A:
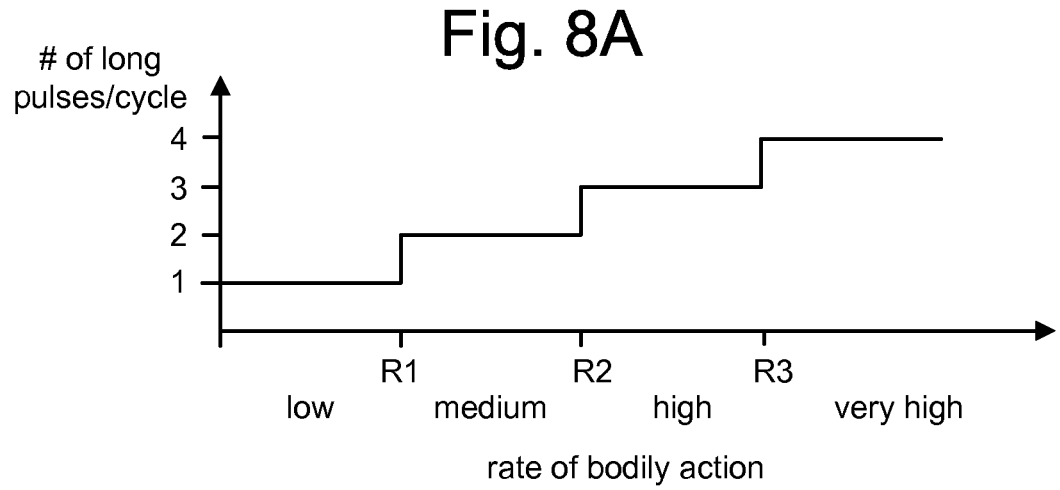
FIG. 8A depicts a technique for adaptively setting the number of long pulses per cycle based on rate of a bodily action.

FIG. 8A depicts a technique for adaptively setting the number of long pulses per cycle based on rate of a bodily action. Adaptively setting the number of long pulses in each cycle can enable the receiver to determine the rate of bodily action more accurately. For example, more long pulses can be provided per cycle when the rate of the bodily action is higher, than when the rate of the bodily action is lower. In this way, the receiver receives the long pulses more frequently, so it can detect changes in the rate sooner and can synchronize to the long pulses more reliably. For instance, it can be easier and more reliable to synchronize to three consecutive long pulses than to two when there is a high. At other times, when the rate is lower, two long pulses may be sufficient for synchronization, and power is saved by transmitting two long pulses instead of three. A similar benefit can be achieved when the adaptive setting is based on a rate of change of the bodily action.

In one possible approach, multiple categories of rates are set, e.g., low, medium, high and very high. For a heart rate (HR), for instance, the low category may be defined by $HR \leq R1$, the medium category may be defined by $R1 < HR \leq R2$, the high category may be defined by $R2 < HR \leq R3$, and the very high category may be defined by $R3 < HR$. As an example, $R1 = 60$ beats per minute, $R2 = 120$ beats per minute and $R3 = 180$ beats per minute. In one possible implementation, one, two, three or four long pulses are provided in each cycle when the heart rate is in the low, medium, high or very high category, respectively. Appropriate values for the boundaries of the categories, R1, R2 and R3 can be determined by experimentation. The range of rates in the different categories can be the same or different.

In another example, implementation, at least two long pulses are provided in each cycle. In this case, two, three, four or five long pulses can be provided in each cycle when the heart rate is in the low, medium, high or very high category, respectively.

Figure 8B:
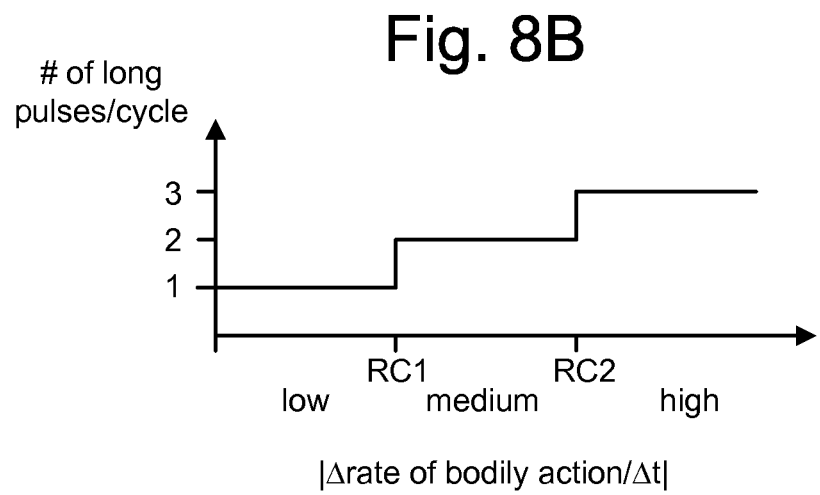
FIG. 8B depicts a technique for adaptively setting the number of long pulses per cycle based on a rate of change of a bodily action.

FIG. 8B depicts a technique for adaptively setting the number of long pulses per cycle based on a rate of change of a bodily action. By using an absolute value of the rate of change of a bodily action, the receiver can respond more reliably during increases and decreases in the rate of the bodily action, such as by updating a display to represent the current rate. In one possible approach, multiple categories of the rate of change are set, e.g., low, medium and high. For the rate of change (RC), the low category may be defined by $RC \leq RC1$, the medium category may be defined by $RC1 < RC \leq RC2$, and the high category may be defined by $RC2 < RC$. In one possible implementation, one, two or three long pulses are provided in each cycle when the rate of change is in the low, medium or high category, respectively. Appropriate values for the boundaries of the categories, RC1 and RC2 can be determined by experimentation, and knowledge of the maximum practical rates of change which are experienced with a human subject, for instance. As an example a maximum change in heart rate is about 15% in 5 sec. for a human. The ranges of rates of change in the different categories can be the same or different. Also, instead of using the absolute value of the rate of change, different categories can be defined for positive and negative rates of change.

In another example implementation, at least two long pulses are provided in each cycle. In this case, two, three or four long pulses can be provided in each cycle when the rate of change is in the low, medium or high category, respectively.

Generally, the rate of change is the first derivative of the rate. The concept can be extended to higher order derivatives of the rate.

Figure 9A:
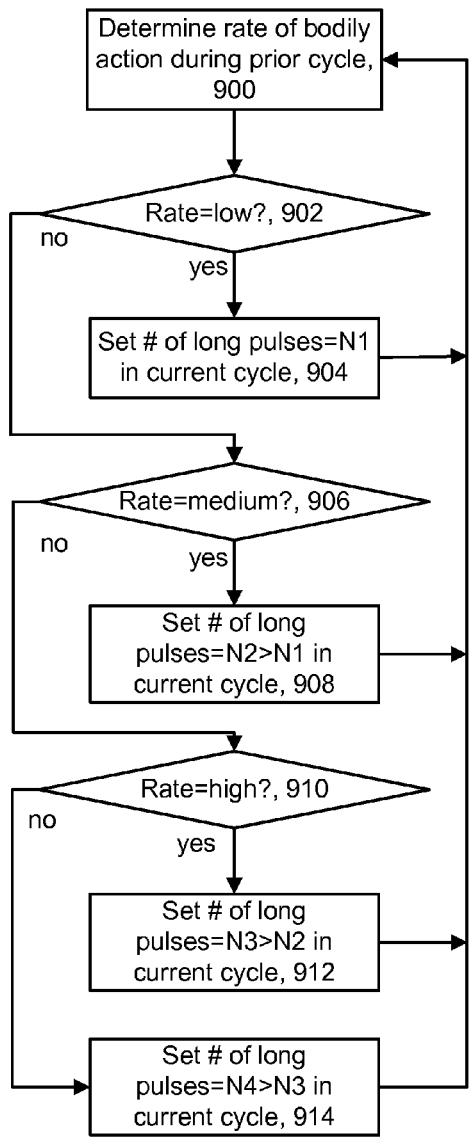
FIG. 9A depicts details of an example method used by step 608 of FIG. 6 to set the number of long pulses used in a cycle based on a rate of a bodily action.

FIG. 9A depicts details of an example method used by step 608 of FIG. 6 to set the number of long pulses used in a cycle based on a rate of a bodily action. As mentioned in connection with step 608, the microprocessor can employ logic to determine when to transmit a long or short pulse. In one example adaptive approach, step 900 includes determining a rate of a bodily action during a prior cycle. For example, this may occur at the start of a current cycle in which a decision is made as to how many long pulses to use in the current cycle. The rate can be determined in different ways. One way is to determine an average rate for the entire prior cycle. For instance, if there are five pulses per cycle, and a cycle duration is 5 sec., the average rate is 5 beats/5 sec.=1 beat/sec. Another way is to determine the rate based on the last two beats in the cycle. Another way is to determine the rate for each beat, and use the last two beats if the associated rate is consistent with the rate of the previous beats, e.g., within a specific percentage such as +/−10%. Another way is to determine the rate based on the last M1 beats in the cycle, where $M1 \geq 2$ and M1 is less than the total number of beats in the cycle. Another way is to divide the cycle into two or more subsets of beats, determine an average rate for each subset, and determine an average among the rates of the different subsets. Another way is to determine the rate based on the last M2 cycles, where $M2 \geq 2$. Moreover, various filtering techniques can be used to smooth the rate. Other approaches are possible as well.

At decision step 902, if the rate is in the low category, the number of long pulses is set to a number N1 for the current cycle at step 904. In one approach, $N1 \geq 1$. In another approach which allows the receiver to synchronize to long pulses in one cycle, $N1 \geq 2$. At decision step 906, if the rate is in the medium category, the number of long pulses is set to a number $N2 > N1$ for the current cycle at step 908. At decision step 910, if the rate is in the high category, the number of long pulses is set to a number $N3 > N2$ for the current cycle at step 912. Otherwise, the rate is in the very high category, and the number of long pulses is set to a number $N4 > N3$ for the current cycle at step 914. Having determined the number of long pulses to use in the current cycle, the current cycle begins. Example waveforms are discussed in connection with FIGS. 10A-10D.

Figure 9B:
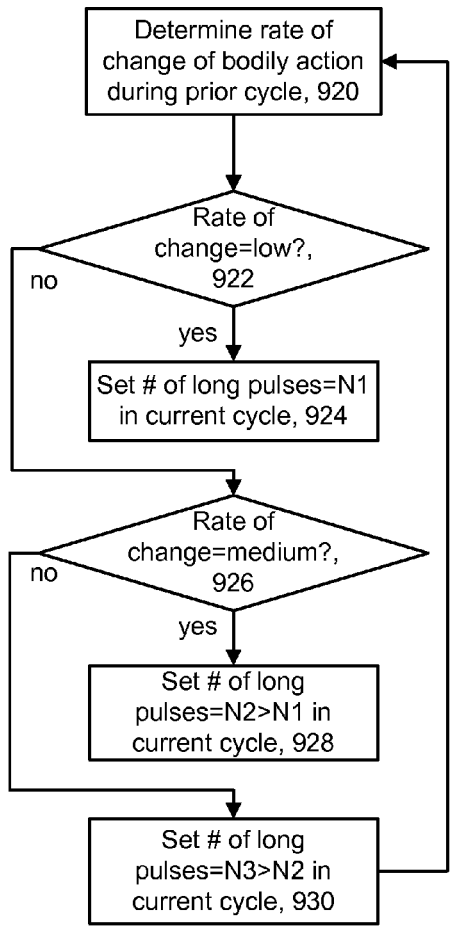
FIG. 9B depicts details of an example method used by step 608 of FIG. 6 to set the number of long pulses used in a cycle based on a rate of change of a bodily action.

FIG. 9B depicts details of an example method used by step 608 of FIG. 6 to set the number of long pulses used in a cycle based on a rate of change of a bodily action. Step 920 includes determining a rate of change of a bodily action during a prior cycle. For example, this may occur at the start of a current cycle in which a decision is made as to how many long pulses to use in the current cycle. The rate of change can be determined in different ways. One way is to determine an average rate of change for the entire prior cycle by determining a rate of change between the first and last beats in the prior cycle. For instance, if there are five pulses per cycle, the first beat has a rate of 1 beat per second, and the last beat is 5 sec. later and has a rate of 1.1 beats/sec., the rate of change is [(1.1−1)beats/sec.]/5 sec.=0.02 beats/sec.$^2$.

Another way is to determine the rate of change based on the last two beats in the cycle. Another way is to determine the rate of change for each beat, and use the last two beats if the associated rate is consistent with the rate of the previous beats, e.g., within a specific percentage such as +/−10%. Another way is to determine the rate of change based on the last M1 beats in the cycle, where $M1 \geq 2$ and M1 is less than the total number of beats in the cycle. Another way is to divide the cycle into two or more subsets of beats, determine an average rate of change for each subset, and determine an average among the rates of change of the different subsets. Another way is to determine the rate of change based on the last M2 cycles, where $M2 \geq 2$. Moreover, various filtering techniques can be used to smooth the rate of change. Other approaches are possible as well.

At decision step 922, if the rate of change is in the low category, the number of long pulses is set to a number N1 for the current cycle at step 924. In one approach, $N1 \geq 1$. In another approach which allows the receiver to synchronize on long pulses in one cycle, $N1 \geq 2$. At decision step 926, if the rate of change is in the medium category, the number of long pulses is set to a number N2>N1 for the current cycle at step 928. Otherwise, the rate of change is in the high category, and the number of long pulses is set to a number N3>N2 for the current cycle at step 930. Having determined the number of long pulses to use in the current cycle, the current cycle begins. Example waveforms are discussed in connection with FIGS. 11A and 11B.

Figure 10A:
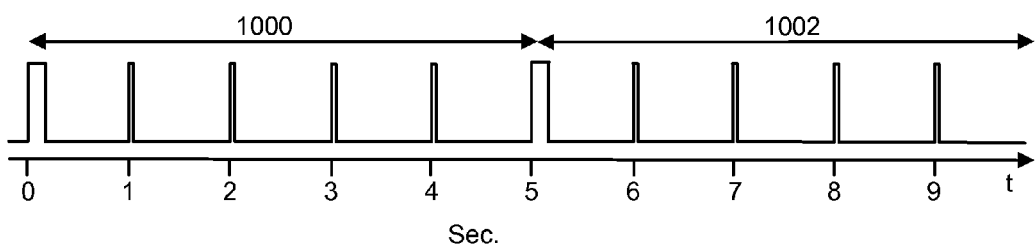
FIG. 10A depicts a time line of a wireless signal transmitted by a monitor, where a single long pulse is used in a cycle, when a rate of a bodily action is low.

FIG. 10A depicts a time line of a wireless signal transmitted by a monitor, where a single long pulse is used in a cycle, when a rate of a bodily action is low. Each cycle 1000, 1002 includes five pulses, including one long pulse as the first pulse. The time lines are consistent in FIGS. 10A-10D. This example indicates a steady rate of 1 beat/sec. (60 beats/min.), and may correspond to the low category of FIG. 8A, for instance.

Figure 10B:
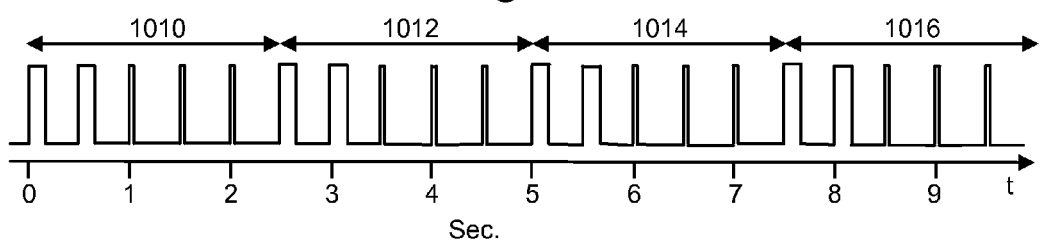
FIG. 10B depicts a time line of a wireless signal transmitted by a monitor, where two consecutive long pulses are used in a cycle, when a rate of a bodily action is medium.

FIG. 10B depicts a time line of a wireless signal transmitted by a monitor, where two consecutive long pulses are used in a cycle, when a rate of a bodily action is medium. Cycles 1010, 1012, 1014 and 1016 each include five pulses, including two long pulses as the first and second pulses. This example indicates a steady rate of 2 beat/sec. (120 beats/min.), and may correspond to the medium category of FIG. 8A, for instance.

Figure 10C:
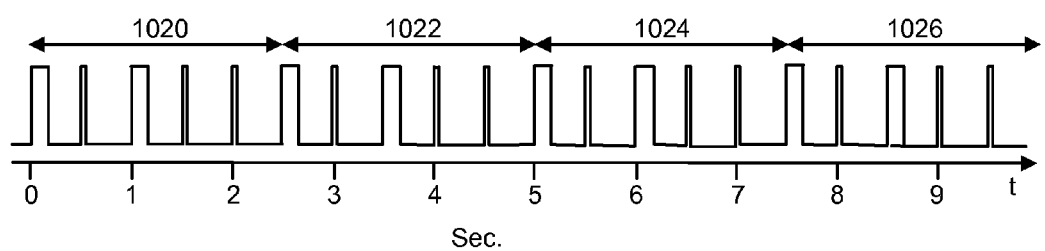
FIG. 10C depicts a time line of a wireless signal transmitted by a monitor, where two non-consecutive long pulses are used in a cycle, when a rate of a bodily action is medium, as an alternative to FIG. 10B.

FIG. 10C depicts a time line of a wireless signal transmitted by a monitor, where two non-consecutive long pulses are used in a cycle, when a rate of a bodily action is medium, as an alternative to FIG. 10B. Cycles 1020, 1022, 1024 and 1026 each include five pulses, including two long pulses as the first and third pulses. This example also indicates a steady rate of 2 beats/sec. (120 beats/min.), and may correspond to the medium category of FIG. 8A, for instance. Although the long pulses can be provided consecutively, such as at the beginning of the cycle, this is not necessary. For example, the long pulses can be provided according to any predetermined pattern which can be recognized by, and is known to, the receiver. For instance, the long pulses can be provided as every other pulse, as shown here.

Figure 10D:
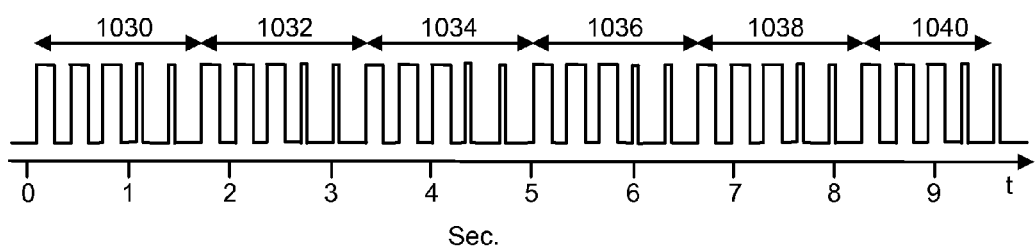
FIG. 10D depicts a time line of a wireless signal transmitted by a monitor, where three consecutive long pulses are used in a cycle, when a rate of a bodily action is high.

FIG. 10D depicts a time line of a wireless signal transmitted by a monitor, where three consecutive long pulses are used in a cycle, when a rate of a bodily action is high. Cycles 1030, 1032, 1034, 1036, 1038 and 1040 each include five pulses, including three long pulses as the first, second and third pulses. This example also indicates a steady rate of 3 beat/sec. (180 beats/min.), and may correspond to the high category of FIG. 8A, for instance.

Alternatively, when it is desired to have at least two long pulses in each cycle, FIG. 10A can use two long pulses per cycle, FIGS. 10B and 10C can use three long pulses per cycle, and FIG. 10D can use four long pulses per cycle.

FIG. 11A depicts a time line of a wireless signal transmitted by a monitor, where a number of long pulses used in a cycle is adjustable based on a rate of change of a bodily action. Cycles 1100, 1102, 1104 and 1106 each include five pulses. However, cycle 1100 includes one long pulse as the first pulse, cycles 1102 and 1104 each includes two long pulses as the first and second pulses, and cycle 1106 includes three long pulses as the first, second and third pulses. This example shows how the rate of change can vary in different cycles. The rate itself can vary in different cycles as well but the waveforms of FIGS. 10A-10D were shown as each having a fixed rate for simplicity.

This example is meant to show that the rate of change generally increases in cycles 1100 and 1104, and is generally constant in cycle 1104. FIG. 11B depicts a rate of change of a bodily action, consistent with FIG. 11A. The solid line indicates the rate of change. For cycle 1100, the prior cycle is assumed to have a rate of change in the low category of FIG. 8B (with RC<RC1), for instance, so that one long pulse is provided in cycle 1100. The rate of change of cycle 1100 also starts out with RC<RC1. The rate of change is calculated for each pulse in this example. However, at around time=2 sec., the rate of change exceeds RC1. At the start of the cycle 1102, we assume that the rate of change for the prior cycle 1100 is determined to be between RC1 and RC2, in the medium category of FIG. 8B, so that two long pulses are used in cycle 1102. The rate of change continues at a steady pace between RC1 and RC2 in cycle 1102, so that at the start of the cycle 1104, we assume that the rate of change for the prior cycle 1102 is determined to be between RC1 and RC2, in the medium category of FIG. 8B, so that two long pulses are used in the cycle 1104. During cycle 1104, the rate of change increase above RC2 at around 6.5 sec., so that at the start of the cycle 1106, we assume that the rate of change for the prior cycle 1104 is determined to be above RC2, in the high category of FIG. 8B, so that three long pulses are used in the cycle 1106.

Alternatively, when it is desired to have at least two long pulses in each cycle, cycle 1100 can use two long pulses, cycles 1102 and 104 can use three long pulses, and cycle 1106 an use four long pulses.

The foregoing detailed description of the technology herein has been presented for purposes of illustration and description. It is not intended to be exhaustive or to limit the technology to the precise form disclosed. Many modifications and variations are possible in light of the above teaching. The described embodiments were chosen to best explain the principles of the technology and its practical application to thereby enable others skilled in the art to best utilize the technology in various embodiments and with various modifications as are suited to the particular use contemplated. It is intended that the scope of the technology be defined by the claims appended hereto.

We claim:

1. A user-worn monitor, comprising:
an amplifier circuit, the amplifier circuit receives a signal regarding a bodily action of a user and provides a corresponding amplified signal;
a microcontroller associated with the amplifier circuit; and
a transmitter associated with the microcontroller and the amplifier circuit, the transmitter provides a wireless signal based on the amplified signal, the wireless signal includes respective pulses in successive cycles, where each respective pulse is generated when a respective instance of the bodily action is detected, the respective pulses include identifier pulses which each have a duration which is set in response to the microcontroller to identify the user-worn monitor, the identifier pulses are interspersed among other pulses, and a number N of the identifier pulses in each cycle is set adaptively based on the respective instances of the bodily action, where $N \geq 1$.

2. The user-worn monitor of claim 1, wherein:
each cycle includes a same number of the respective pulses, and at least two of the cycles include different numbers of the identifier pulses.

3. The user-worn monitor of claim 1, wherein:
the number of the identifier pulses in each cycle is set adaptively based on a detected rate of the respective instances of the bodily action.

4. The user-worn monitor of claim 1, wherein:
the number of the identifier pulses in each cycle is set adaptively based on a rate of change of a detected rate of the respective instances of the bodily action.

5. The user-worn monitor of claim 1, wherein:
the identifier pulses are provided in each cycle according to a predetermined pattern.

6. The user-worn monitor of claim 1, wherein:
the transmitter does not provide the wireless signal with pulses at times other than when the bodily action of the user is detected.

7. The user-worn monitor of claim 1, wherein:
each respective instance of the bodily action is at least one of: (a) a heartbeat or (b) a respective instance of a repetitive physical movement performed by the user during exercise.

8. A method for transmitting a wireless signal from a user-worn monitor, comprising:
receiving a signal regarding a bodily action of a user and providing a corresponding amplified signal; and
based on the amplified signal, providing a wireless signal which includes respective pulses in successive cycles, where each respective pulse is generated when a respective instance of the bodily action is detected, the respective pulses include identifier pulses which each have a duration which identifies the user-worn monitor, the identifier pulses are interspersed among other pulses, and a number N of the identifier pulses in each cycle is set adaptively based on the respective instances of the bodily action, where $N \geq 1$.

9. The method of claim 8, wherein:
each cycle includes a same number of the respective pulses, and at least two of the cycles include different numbers of the identifier pulses.

10. The method of claim 8, wherein:
the number of the identifier pulses in each cycle is set adaptively based on a detected rate of the respective instances of the bodily action.

11. The method of claim 8, wherein:
the number of the identifier pulses in each cycle is set adaptively based on a rate of change of a detected rate of the respective instances of the bodily action.

12. The method of claim 8, wherein:
the transmitter does not provide the wireless signal with pulses at times other than when the bodily action of the user is detected.

13. The method of claim 8, wherein:
each respective instance of the bodily action is at least one of: (a) a heartbeat or (b) a respective instance of a repetitive physical movement performed by the user during exercise.

14. The method of claim 8, wherein $N \geq 2$.

15. A receiver unit, comprising:
a receiver circuit, the receiver circuit receives a wireless signal from a user-worn monitor, the wireless signal includes respective pulses generated by the user-worn monitor, each respective pulse is generated when a respective instance of a bodily action of the user is detected, the respective pulses include identifier pulses which each have a duration which identifies the user-worn monitor, the identifier pulses are interspersed among other pulses, and the respective pulses are in successive cycles, where a number N of the identifier pulses in each cycle varies based on the respective instances of the bodily action, where $N \geq 2$;
an amplifier circuit associated with the receiver circuit, the amplifier circuit provides an amplified signal based on the wireless signal;
a microprocessor associated with the amplifier circuit, the microprocessor processes the amplified signal to interpret the duration of each of the identifier pulses as an identifier of the user-worn monitor, and in each cycle: (a) synchronizes with the identifier pulses, and (b) determines a rate of the bodily action based on: (i) time intervals between the identifier pulses and (ii) a number of the other pulses between each of the identifier pulses; and
an output device associated with the microprocessor, the output device provides an output based on the rate of the bodily action.

16. The receiver unit of claim 15, wherein:
the microprocessor interprets the duration of each of the identifier pulses as the identifier of the user-worn monitor based on the duration of each of the identifier pulses being consistent with a predefined set of different durations which are available identifiers for different user-worn monitors.

17. The receiver unit of claim 15, wherein:
the wireless signal does not contain pulses generated by the user-worn monitor at times other than when the bodily action of the user is detected.

18. The receiver unit of claim 15, wherein:
each cycle includes a same number of the respective pulses, and at least two of the cycles include different numbers of the identifier pulses.

19. The receiver unit of claim 15, wherein:
the number of the identifier pulses in each cycle varies adaptively based on a detected rate of the respective instances of the bodily action.

20. The receiver unit of claim 15, wherein:
the number of the identifier pulses in each cycle varies adaptively based on a rate of change of a detected rate of the respective instances of the bodily action.

* * * * *